(12) United States Patent
Wyss et al.

(10) Patent No.: US 9,744,295 B2
(45) Date of Patent: Aug. 29, 2017

(54) ROTATABLE INFUSION SET

(71) Applicant: Roche Diagnostics International AG, Steinhausen (CH)

(72) Inventors: Martin Wyss, Burgdorf (CH); Simon Scheuer, Bern (CH); Reto Aeschilmann, Aefligen (CH); Christian Thalmann, Kehrsiten (CH)

(73) Assignee: Roche Diagnostics International AG, Steinhausen (CH)

( * ) Notice: Subject to any disclaimer, the term of this patent is extended or adjusted under 35 U.S.C. 154(b) by 20 days.

(21) Appl. No.: 14/948,714

(22) Filed: Nov. 23, 2015

(65) Prior Publication Data

US 2016/0121046 A1 May 5, 2016

Related U.S. Application Data

(60) Division of application No. 12/329,242, filed on Dec. 5, 2008, now Pat. No. 9,216,250, which is a (Continued)

(30) Foreign Application Priority Data

Jun. 7, 2006 (CH) .......................... 911/06

(51) Int. Cl.
  *A61M 5/158* (2006.01)
  *A61M 39/10* (2006.01)
(52) U.S. Cl.
  CPC ......... *A61M 5/158* (2013.01); *A61M 39/1055* (2013.01); *A61M 2005/1581* (2013.01);
  (Continued)

(58) Field of Classification Search
  CPC .. A61M 2005/1581; A61M 2005/1585; A61M 2005/1586; A61M 2005/1587; A61M 39/1055; A61M 5/158
  See application file for complete search history.

(56) References Cited

U.S. PATENT DOCUMENTS 5,968,011 A * 10/1999 Larsen .................. A61M 5/158
                                                  604/164.01
6,086,575 A    7/2000 Mejslov
(Continued)

FOREIGN PATENT DOCUMENTS

DE      29905068 U1   10/1999
EP       1820525 A1    8/2007
(Continued)

*Primary Examiner* — Bhisma Mehta
*Assistant Examiner* — Brandy S Lee
(74) *Attorney, Agent, or Firm* — Dinsmore & Shohl LLP

(57) ABSTRACT

An arrangement for introducing a liquid into the body of a patient or for withdrawing a liquid from the body of a patient, including a first structural part carrying a cannula for positioning in the body of the patient, and a second structural part with a connection port for detachably coupling a conduit for supplying or withdrawing a liquid, wherein the first and second structural parts are connected, can be rotated relative to each another and in relative rotational positions form a channel for introducing a liquid from the conduit to the cannula or for withdrawing a liquid from the cannula to the conduit, and whereby movement of the conduit for coupling and uncoupling is transverse to the longitudinal axis of the cannula.

17 Claims, 14 Drawing Sheets

Related U.S. Application Data continuation of application No. PCT/CH2007/000074, filed on Feb. 13, 2007.

(52) U.S. Cl.
CPC ............... *A61M 2005/1585* (2013.01); *A61M 2005/1586* (2013.01); *A61M 2005/1587* (2013.01)

(56) References Cited

U.S. PATENT DOCUMENTS

| | | |
|---|---|---|
| 6,923,791 B2 | 8/2005 | Douglas |
| 6,949,084 B2 | 9/2005 | Marggi et al. |
| 2002/0161332 A1 | 10/2002 | Ramey |
| 2005/0020972 A1 | 1/2005 | Horisberger et al. |
| 2005/0101910 A1* | 5/2005 | Bowman ............... A61M 25/02 604/93.01 |
| 2005/0101932 A1 | 5/2005 | Cote et al. |
| 2005/0101933 A1 | 5/2005 | Marrs et al. |
| 2005/0107743 A1 | 5/2005 | Fangrow |
| 2007/0185441 A1 | 8/2007 | Fangrow |

FOREIGN PATENT DOCUMENTS

| | | |
|---|---|---|
| WO | 9858693 A1 | 12/1998 |
| WO | 02070037 A2 | 9/2002 |
| WO | 2004026375 A1 | 4/2004 |
| WO | 2004101071 A2 | 11/2004 |
| WO | 2005049117 A2 | 6/2005 |

\* cited by examiner

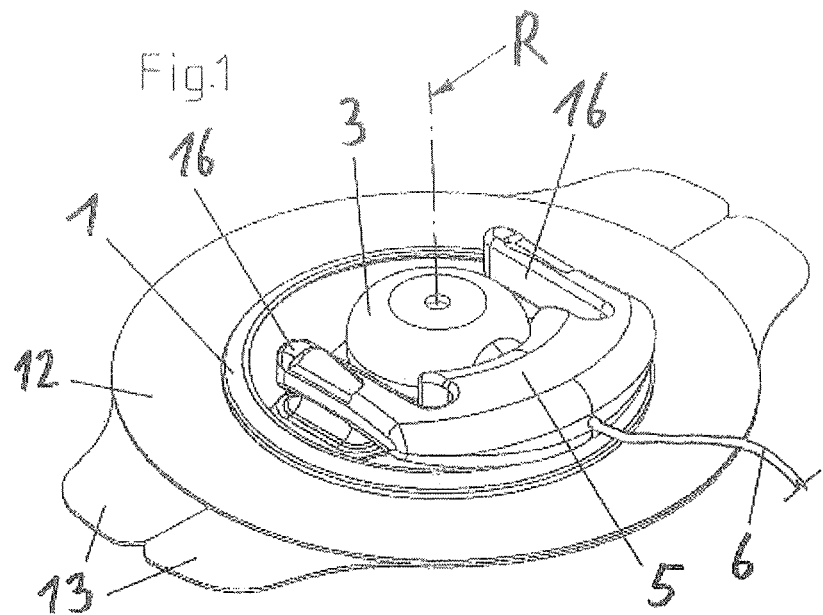
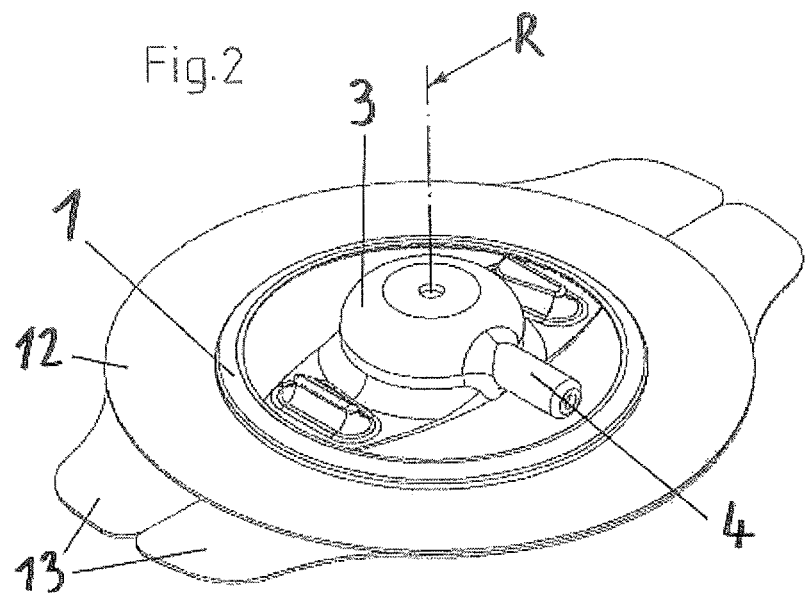

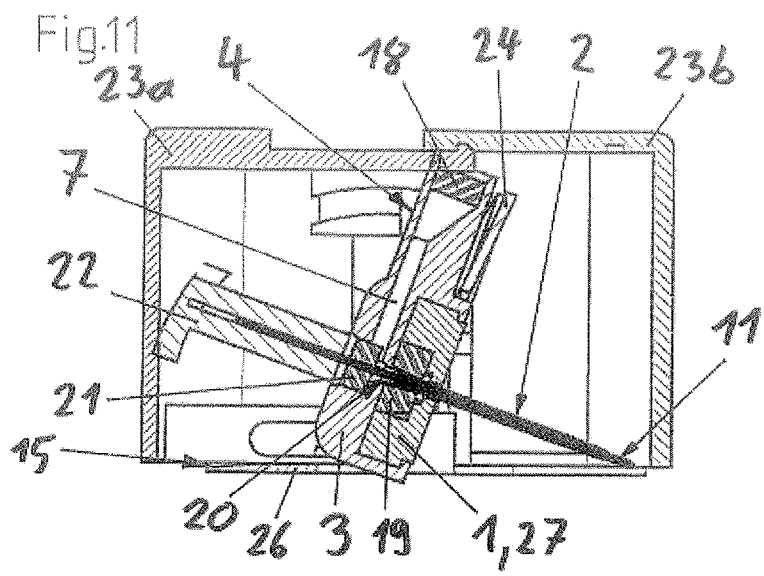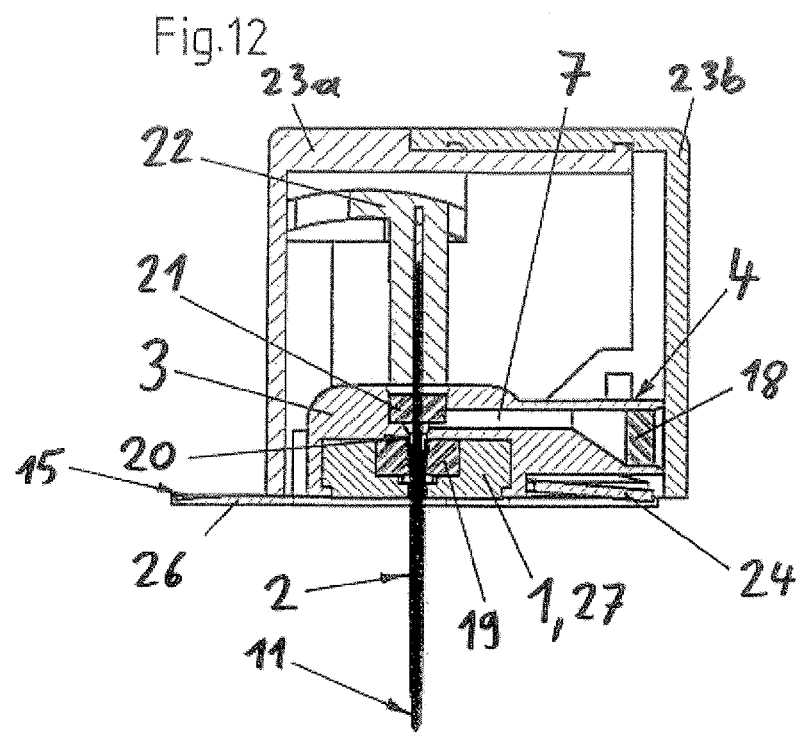

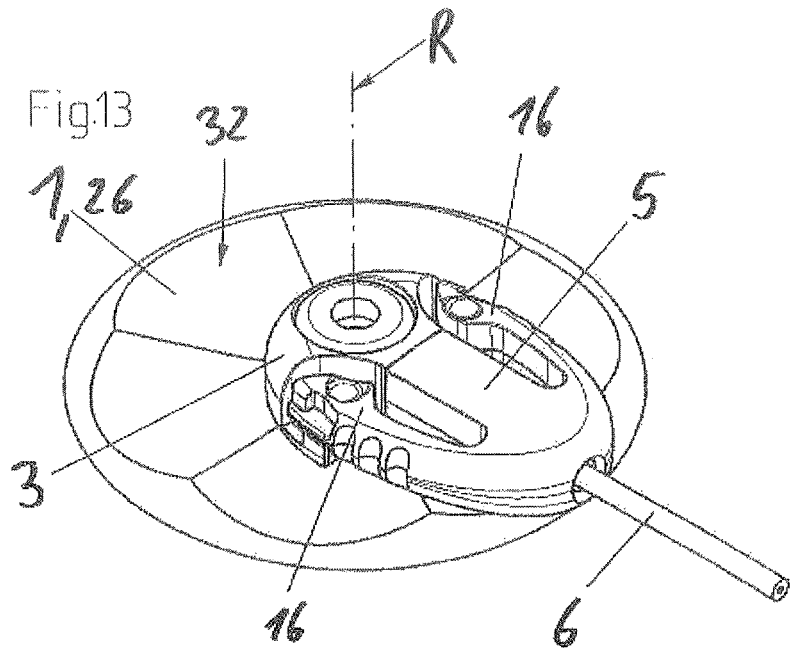
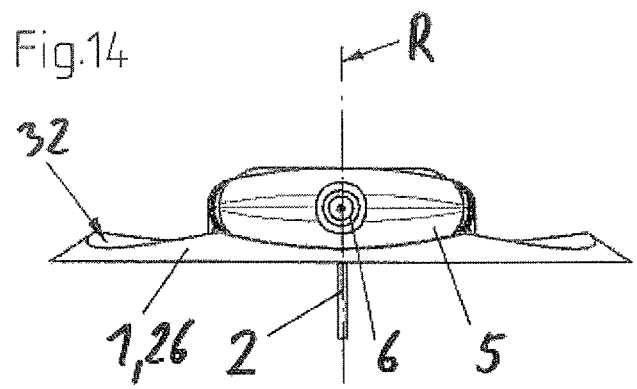

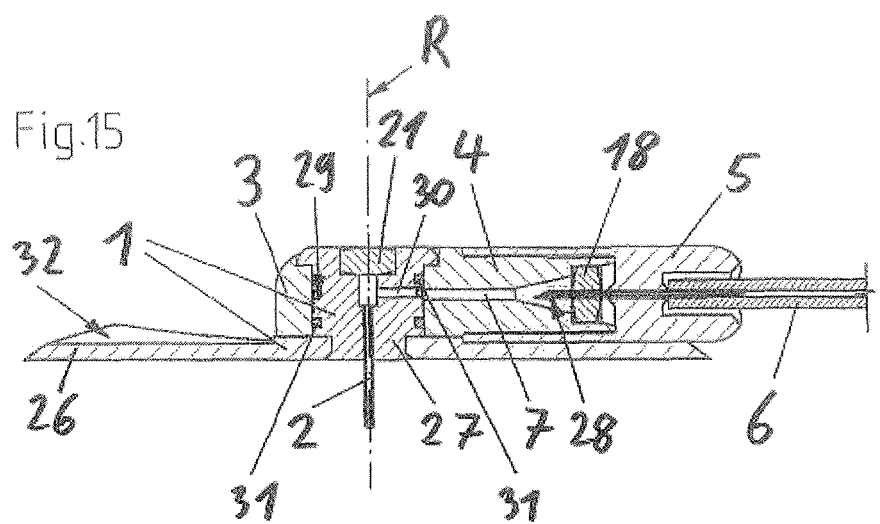

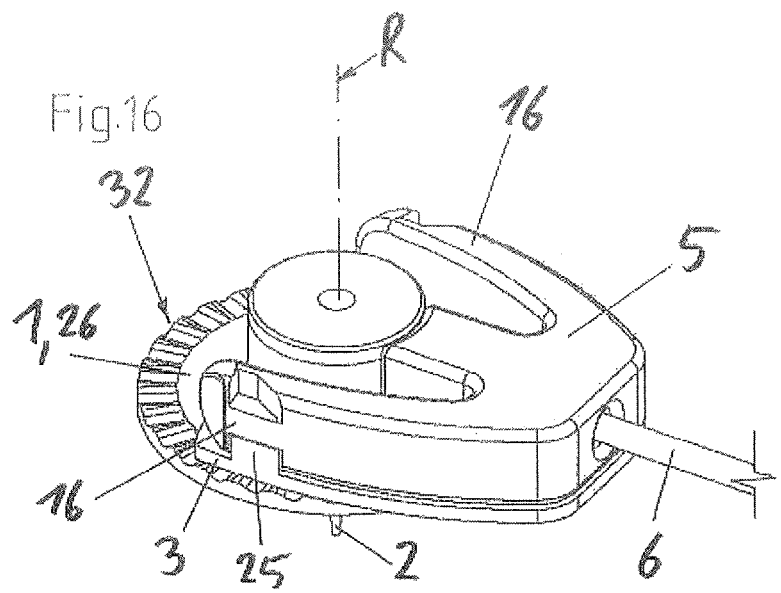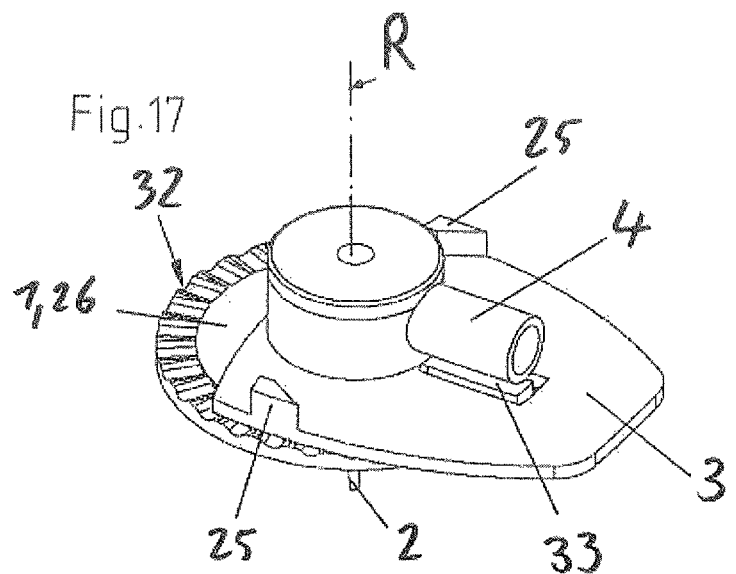

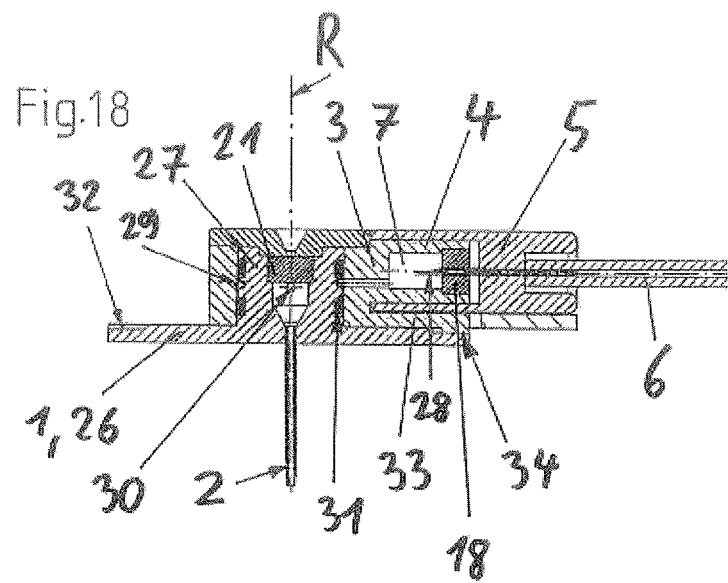

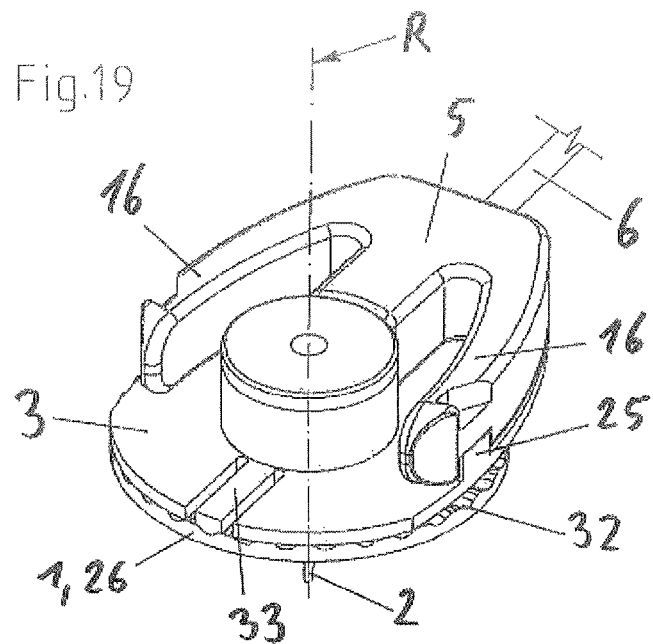
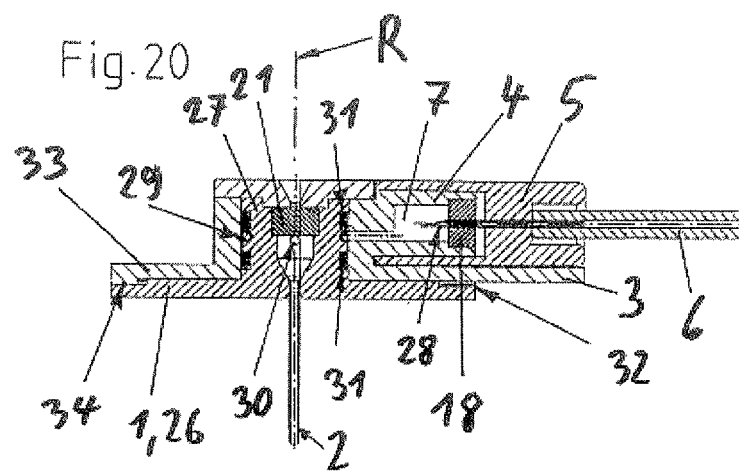

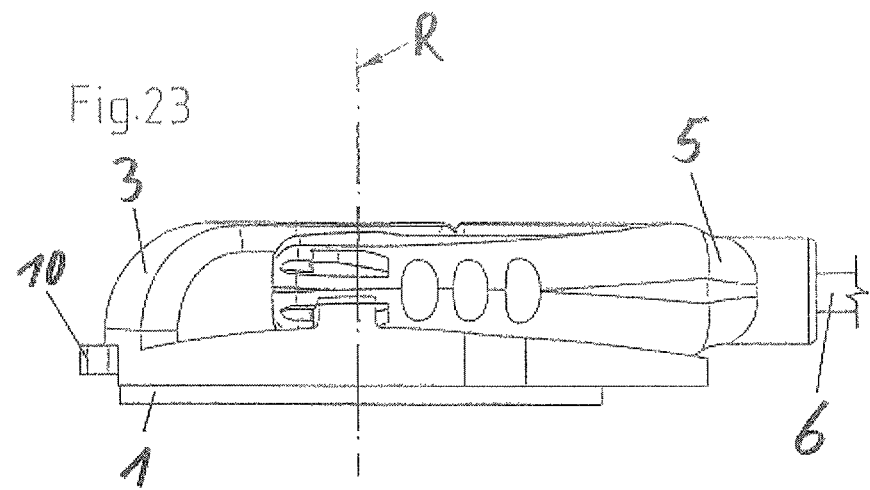
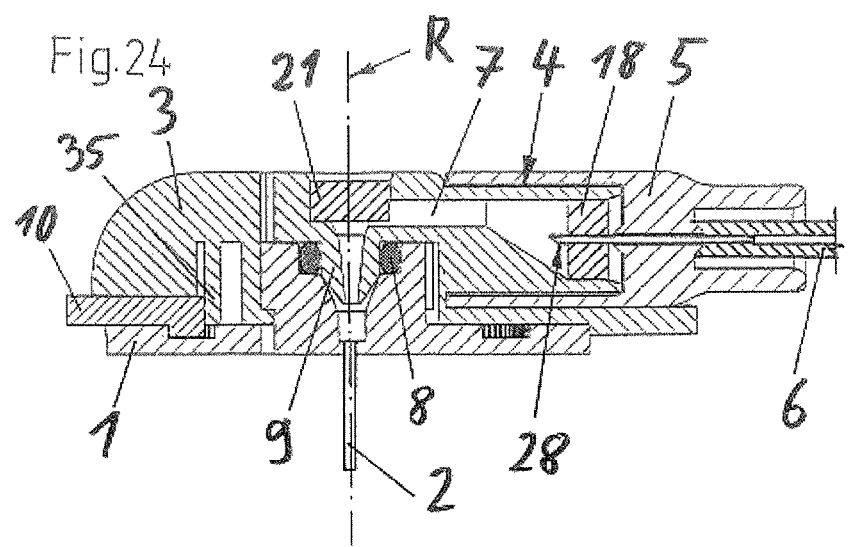

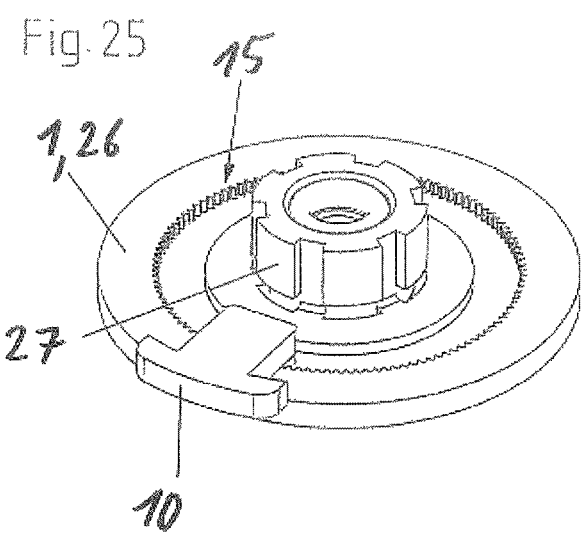

ROTATABLE INFUSION SET

CROSS-REFERENCE TO RELATED APPLICATIONS

This application is a divisional of application Ser. No. 12/329,242 filed Dec. 5, 2008 which is a continuation of International Patent Application No. PCT/CH2007/000074, filed on Feb. 13, 2007, which claims priority to Swiss Application No. 911/06, filed on Jun. 7, 2006, the entire contents of both of which are incorporated herein by reference.

BACKGROUND

The present invention relates to devices for infusing, delivering, administering, injecting or dispensing a substance, and to methods of making and using such devices. More particularly, it relates to an arrangement for introducing a liquid into the body of a patient or for withdrawing a liquid from the body of a patient and use of the arrangement for subcutaneous supplying of a liquid medicament into the body of a patient.

In those patients who have an ongoing need for medicaments or therapeutic agents to be administered by direct supply to the body tissue or the blood stream, or in whom body fluid samples for monitoring certain parameters, such as e.g. blood sugar, need to be taken from the body over a longer period, it is meaningful to undertake supply of the medicament or withdrawal of the body fluid via a cannula introduced at a suitable site into the body and remaining there over a longer period.

For example, these days, in many patients with type I and type II diabetes, the required quantity of insulin is supplied to the body continuously or at short intervals. This may be accomplished, in many instances, using a cannula inserted through the skin into the subcutaneous tissue of the patient, which is part of an arrangement attached to the body of the patient and often designated as an "infusion set." The insulin supplied is controlled by an automated insulin pump. The connection between insulin pump and infusion set is made by a flexible supply conduit which is coupled detachably to the infusion set by a connector. Since the infusion set is worn practically permanently on the body, good wearer comfort is important. For this reason, the infusion set is built as flat as possible, including with a supply conduit connected, and the freedom of movement of the patient is impaired to the least extent possible. In addition, it is important that the coupling and uncoupling of the supply conduit can be done easily and securely and operating errors are excluded as early as possible by the constructive configuration of the infusion set. Similar marginal conditions and requirements will emerge when body fluid samples are taken from the body of a patient over a longer period.

Documents WO 02/070037 A2, DE 299 05 068 U1, U.S. Pat. No. 6,923,791 B2, WO 2005/049117 A2, US 2005/0101910 A1 and WO 2004/026375 A1 disclose infusion devices in which the supply conduit with an adapter part in an axial direction of the cannula can be set on the part of the device bearing the cannula and can be removed again from the latter in the opposite direction. The cannula in the infusion devices disclosed in WO 02/070037 A2, U.S. Pat. No. 6,923,791 B2, WO 2005/049117 A2, US 2005/0101910 A1 and WO 2004/026375 A1 are provided for substantially vertical insertion into the body of the patient, whereby the supply conduit is led away from the adapter part in a direction vertical to the direction of setting. The device disclosed in DE 299 05 068 U1 is provided for inserting into the body of a patient at a flat angle, whereby the supply conduit is led away from the adapter part in the direction of setting. After being set on the part bearing the cannula, the adapter part in the devices according to WO 02/070037 A2, DE 299 05 068 U1, U.S. Pat. No. 6,923,791 B2, WO 2005/049117 A2, US 2005/0101910 A1 is rotatable relative to the part bearing the cannula, while in the device disclosed in WO 2004/026375 A1 it is latched in rotatory alignment selected for setting on with respect to the part bearing the cannula.

A disadvantage of known devices is that the adapter for uncoupling the supply conduit from the infusion set in the axial direction of the cannula is removed from the infusion set, whereby there is a not insubstantial danger that the cannula may be withdrawn from the injection site unnoticed fully or partially, resulting in no delivery or inadequate delivery of liquid medicament into the tissue.

A further disadvantage of the infusion devices disclosed in WO 02/070037 A2, U.S. Pat. No. 6,923,791 B2, WO 2005/049117 A2, US 2005/0101910 A1 and WO 2004/026375 A1 is that, in the applied state with the supply conduit coupled, they have a relatively high structure. An added disadvantage of the device disclosed in DE 299 05 068 U1 is that after application of the part bearing the cannula on the body of a patient there is no further possibility of altering the direction in which the supply conduit leads away from the infusion device.

SUMMARY

An object of the present invention, therefore, is to provide an arrangement for introducing a liquid into the body of a patient or for withdrawing a liquid from the body of a patient, which does not have the disadvantages of the prior art or at least partially avoids these.

In one embodiment, the present invention comprises an arrangement for introducing a liquid into the body of a patient or for withdrawing a liquid from the body of a patient, including a first structural part carrying a cannula for positioning in the body of the patient, and a second structural part with a connection port for detachably coupling a conduit for supplying or withdrawing a liquid, wherein the first and second structural parts are connected, can be rotated relative to each another and, in relative rotational positions, form a channel for introducing a liquid from the conduit to the cannula or for withdrawing a liquid from the cannula to the conduit, and wherein movement of the conduit for coupling and uncoupling is transverse to the longitudinal axis of the cannula.

In one embodiment, the present invention comprises an arrangement for introducing a liquid to the body of a patient or for withdrawing a liquid from the body of a patient, comprising a first structural part with a cannula protruding from this for arrangement in the body of the patient; a second structural part with a connection port for detachable coupling of a corresponding connector of a conduit for supplying or withdrawing a liquid, wherein the first structural part and the second structural part are configured and connected to one another such that they are inseparable and can be rotated relative to one another and in every relative position form a channel for introducing a liquid from the connection port to the cannula or for withdrawing a liquid from the cannula to the connection port, and wherein the connection port of the second structural part is designed such that the coupling and uncoupling of a corresponding connector takes place in each case in a direction transverse to the longitudinal axis of the cannula.

In one embodiment, the present invention comprises an arrangement for introducing a liquid into the body of a patient or respectively for withdrawing a liquid from the body of a patient comprising a first structural part which bears a projecting cannula provided for positioning in the body of a patient after it is inserted in through the skin. The arrangement of the present invention further comprises a second structural part which forms a connection port for detachable coupling of a corresponding connector of a conduit for delivering or withdrawing a liquid. "Corresponding" connector is understood here as a connecting element adapted to complement the connection port, such that the connection port and the connector together form a secure and repeatedly detachable and reconnectable coupling site for the liquid conduit in the form of a matching plug and socket connection. The first structural part and the second structural part of the inventive arrangement are configured and connected to one another such that they are inseparable and can be rotated about an axis of rotation relative to one another. The first and the second structural part, in each relative position which they can take up relative to one another, form a channel sealed to the outside between the connection port and the cannula, via which a liquid can be delivered from the connection port to the cannula or from the cannula to the connection port. The connection port is in this case configured and associated with the second structural part such that the coupling and uncoupling of a corresponding connector of a conduit is possible exclusively in a direction transverse to the longitudinal axis of the cannula.

The present invention enables manufacture of arrangements for introducing a liquid into the body of a patient or respectively for withdrawing a liquid from the body of a patient which offer a high degree of wearer comfort along with good security against operating errors.

In one preferred embodiment of the arrangement of the present invention, the connection port of the second structural part of the arrangement is configured such that the coupling and uncoupling of a corresponding connector in each case must take place vertically to the longitudinal axis of the cannula. This provides maximal security against unintentional withdrawal of the cannula when the connector is being uncoupled.

In yet another preferred embodiment of the arrangement of the present invention, the first and the second structural part can be rotated relative to one another about an axis of rotation extending parallel to the longitudinal axis of the cannula. Thus, a simple construction can be realized, e.g. whenever the cannula is provided for vertical insertion into a body, which may be preferred.

In yet another preferred embodiment of the arrangement in accordance with the present invention, the cannula projects vertically or non-vertically from a substantially even or flat outside surface of the first structural part, whereby in both cases the first and the second structural part can be rotated relative to one another about an axis of rotation standing vertically to the outside surface. The advantage of this is that the rotation plane of the second structural part on completion of application of the arrangement extends parallel to the body surface, so that a substantially identical application situation arises from every rotatory relative position between the first and the second structural part.

In yet another preferred embodiment of the arrangement in accordance with the present invention, the first and the second structural part can be rotated through 360°, e.g. endlessly rotatably about one another, or can be rotated by less than 360° to one another, i.e. not endlessly rotatably about one another. Depending on the application or intended use, one or the other variant can be advantageous, whereby the first-mentioned variant has the advantage that the second structural part can be arranged in every position and that with first and second structural parts endlessly rotatable about one another and corresponding configuration of the arrangement, rotation of the second structural part can occur in any other relative position in any direction of rotation. An advantage of the latter variant, for example, is that unwanted "coiling" of the conduit is not possible with use as intended connected to the arrangement as a result of repeated rotation of the second structural part relative to the first structural part.

In yet another preferred embodiment, the connection between the first and the second structural part is configured such that a specific torque must be overcome for counter-rotation of both structural parts relative to one another, e.g. a torque in the range between 0.01 and 0.05 Nm or in the range between 0.01 and 0.1 Nm. In some preferred embodiments, a pre-tensed elastic structural part is available to generate the torque to be overcome, which produces friction between the first and the second structural part. Exemplary suitable structural parts are a pre-tensed elastic seal, such as an O-ring seal, and/or a ratchet arrangement.

The advantage of such embodiments is that unnecessary rotating, caused e.g. by a change in position of the person wearing the arrangement with respect to the direction of gravity, of both structural parts relative to one another can be prevented, whereby the previously mentioned danger of "coiling" of a liquid conduit coupled to the arrangement is reduced. Retrieval of the connection port after momentary uncoupling of the connector of the connection conduit from the arrangement is also improved, since the second structural part, in the absence of forces bearing thereon, remains in the position assumed during uncoupling relative to the first structural part.

In yet another preferred embodiment, an arrangement in accordance with the present invention comprises a detent means, e.g., a latch or lock, configured for releasably preventing or overriding the twisting capacity (or turning or rotation) of the first and second structural part relative to one another by latching them in a specific position relative to one another.

In some preferred embodiments, the detent means is configured such that the first and the second structural part are latched automatically in a position relative to one another. This may be the case if, for example, no corresponding connector of a conduit is coupled to the connection port of the second structural part. In some embodiments, both structural parts are latched during uncoupling of the connector. In some embodiments, the latching can be cancelled by coupling of a corresponding connector to the connection port, e.g. by a latching element of the latching device being moved by the connector into a non-latched position. Such configuration guarantees easy retrieval of the connection port following momentary uncoupling of the connector from the arrangement, since the second structural part remains in its relative position assumed during uncoupling.

In some preferred embodiments, the detent means is configured such that the first and second structural part are latched or are being latched in a position relative to one another if a corresponding connector of a conduit is coupled or is being coupled to the connection port of the second structural part. Such latching can be cancelled by uncoupling of the connector from the connection port so that there is no latching when the connector is uncoupled. This variant can be advantageous in the event where a selected relative position is to be adhered to in the normal case, e.g. for preventing coiling of the conduit.

In some preferred embodiments, the detent means is configured such that it can be activated and/or deactivated via one or more actuation elements, and, in some embodiments, it may be preferred that the detent means are latched without actuation of the actuation elements. Because of this there is easy retrieval of the connection port following momentary uncoupling of the connector from the arrangement and "coiling" of the coupled conduit is securely prevented. According to one preferred subvariant of the present invention, the detent means can be selectively activated or deactivated via the actuation elements such that, in each state, twisting between the first and the second structural part can be permitted or prohibited.

In embodiments of the arrangement fitted with detent means, the detent means is configured such that latching can take place positively in discrete positions or frictionally in any position. Depending on use and configuration, one or the other of these variants may be preferred.

In yet another preferred embodiment of the arrangement of the present invention, the cannula is designed as a flexible cannula, wherein it is penetrated by a guide needle removable after application by insertion to enable insertion into the tissue of a patient in its cannula channel. Such so-called soft cannulas are well-suited for remaining longer in the subcutaneous tissue of a patient, since they cause almost no irritations in the vicinity of the injection site.

In yet another preferred embodiment of the arrangement of the present invention, the outside surface of the first structural part from which the cannula protrudes extends bears an adhesive layer advantageously formed by plaster for fastening the first structural part by adhesion on the skin of a patient. The adhesive layer is covered by a protective film which is removed shortly prior to application or use of the arrangement. Such an adhesive layer allows the arrangement to be attached securely and comfortably on the skin of the patient during application.

In yet another preferred embodiment, the arrangement additionally comprises a connector for coupling a conduit for delivering or for withdrawing a liquid.

One aspect of the present invention relates to use of the arrangement of the present invention for subcutaneous supplying of a liquid medicament, e.g. for subcutaneous supplying of insulin, into the body of a patient.

BRIEF DESCRIPTION OF THE FIGURES

FIG. 1 is a perspective plan view of an embodiment of an arrangement in accordance with the present invention with a supply conduit connected;

FIG. 2 is a perspective plan view of the embodiment of FIG. 1 with the supply conduit removed;

FIG. 11 is a vertical section through the embodiment illustrated in FIG. 7 in a protective housing;

FIG. 12 is a vertical section through the embodiment illustrated in FIG. 7 directly prior to application or use;

FIG. 13 is a perspective plan view of another embodiment of an arrangement in accordance with the present invention in the applied state with a supply conduit connected;

FIG. 14 is a side elevation of the embodiment of FIG. 13, including of the connecting device of the supply conduit;

FIG. 15 is a vertical section in the longitudinal direction of the supply conduit through the embodiment illustrated in FIG. 13;

FIG. 16 is a perspective plan view of another embodiment of an arrangement in accordance with the present invention in the applied state with a connected supply conduit;

FIG. 17 is a perspective plan view of the embodiment of FIG. 16 without the supply conduit;

FIG. 18 is a vertical section in the longitudinal direction of the supply conduit through the embodiment illustrated in FIG. 16;

FIG. 19 is a perspective plan view of another embodiment of the present invention in the applied state with a connected supply conduit;

FIG. 20 is a vertical section in the longitudinal direction of the supply conduit through the embodiment illustrated in FIG. 19;

FIG. 23 is a side elevation of the embodiment of FIG. 21;

FIG. 24 is a vertical section transverse to the direction of coupling of the supply conduit through the embodiment illustrated in FIG. 21; and FIG. 25 is a perspective view of the first structural part of the embodiment of FIG. 21, including part of the detent means.

DETAILED DESCRIPTION

With regard to fastening, mounting, attaching or connecting components of the present invention, unless specifically described otherwise, conventional mechanical fasteners and methods may be used. Other appropriate fastening or attachment methods include adhesives, welding and soldering, the latter particularly with regard to the electrical system of the invention, if any. In embodiments with electrical features or components, suitable electrical components and circuitry, wires, wireless components, chips, boards, microprocessors, inputs, outputs, displays, control components, etc. may be used. Generally, unless otherwise indicated, the materials for making the invention and/or its components may be selected from appropriate materials such as metal, metallic alloys, ceramics, plastics, etc.

Figure 3:
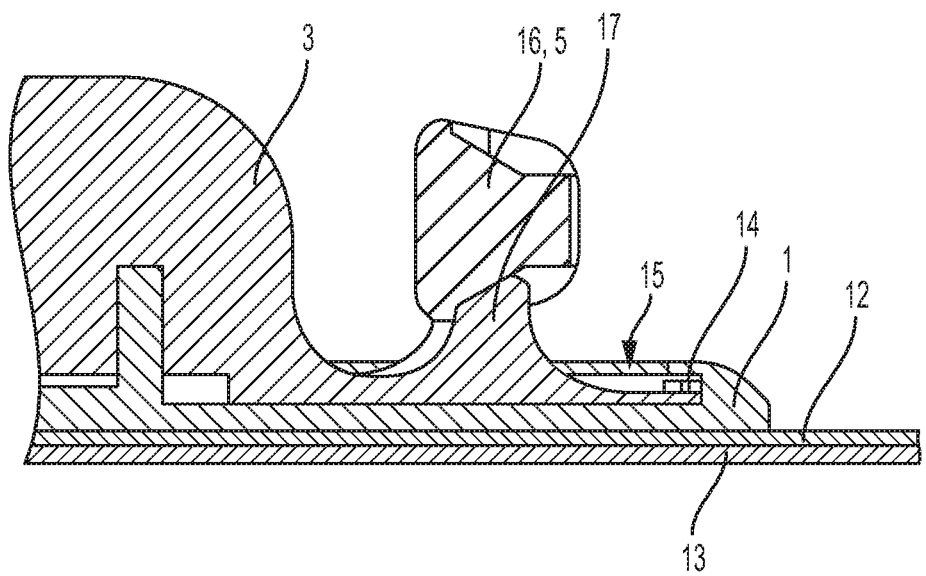
FIG. 3 is a vertical section transverse to the longitudinal direction of the supply conduit through part of the embodiment illustrated in FIG. 1.
Figure 4:
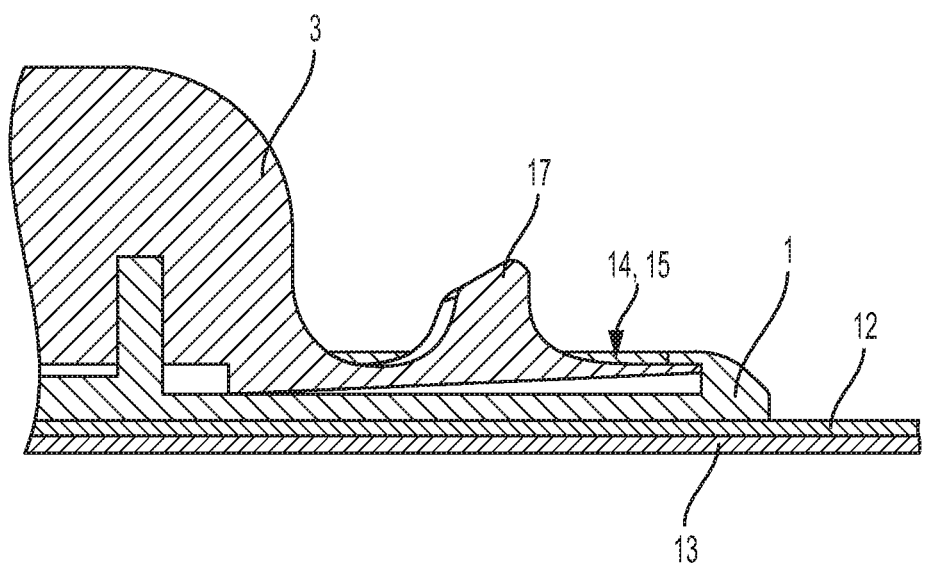
FIG. 4 is an illustration as per FIG. 3 of the embodiment of FIG. 2.
Figure 5:
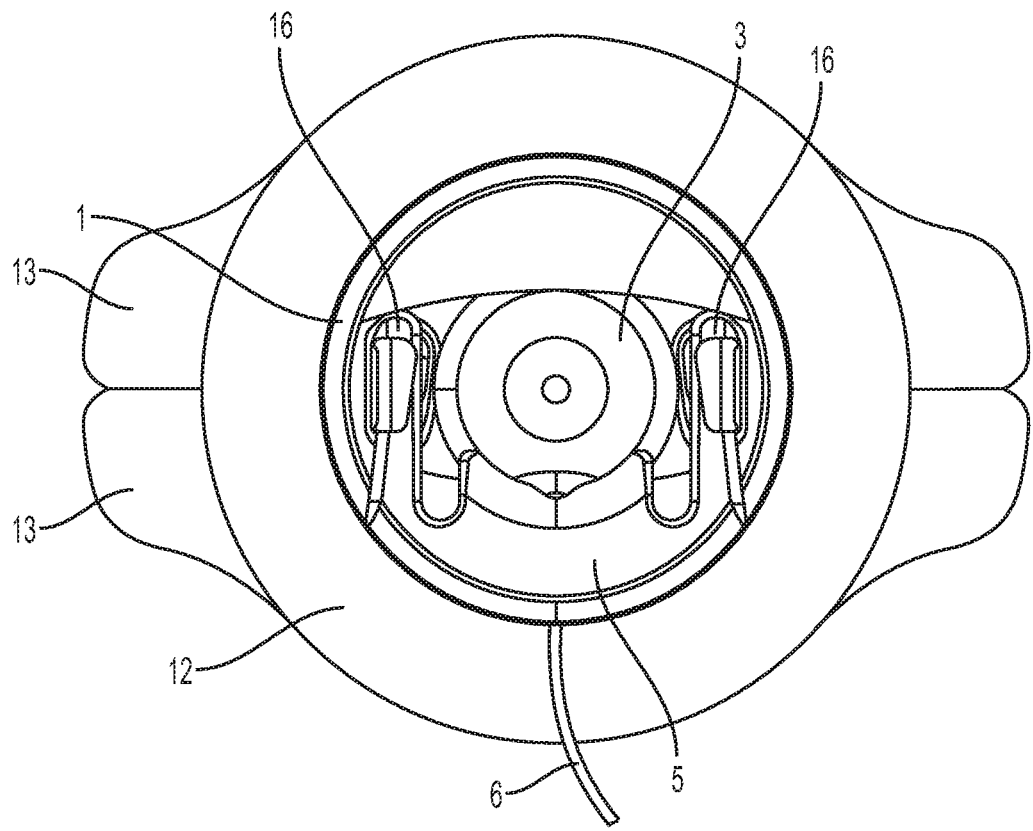
FIG. 5 is a plan view of the embodiment of FIG. 1.

A first preferred embodiment of the inventive arrangement of the present invention (which, in addition to being termed an arrangement, also may be thought of and/or referred to as a system, device, infusion apparatus, infusion set or system) is illustrated in FIGS. 1 and 2 in a perspective plan view, in FIGS. 3 and 4 selectively in the longitudinal section and in FIG. 5 in plan view. This embodiment, in the form of an infusion set, is shown with a coupled supply conduit for an infusion liquid (FIGS. 1, 3 and 5) and also without the supply conduit (FIGS. 2 and 4). The infusion set comprises a first structural part 1, which bears or carries on its underside a vertically projecting cannula (not shown). The underside of the first structural part 1 is formed by plaster 12, the adhesive surface of which is covered by protective plaster paper 13. A second structural part 3 is inseparably connected to the first structural part 1, and can be rotated about a vertical axis of rotation R which runs or extends in the longitudinal axis of the cannula. The second structural part 3 forms a connection port 4 for the connector 5 of the supply conduit 6 and cooperates with the first structural part 1 such that the structural parts, in every rotatory relative position which they can assume relative to one another, form a channel sealed to the exterior (not shown) for delivering the infusion liquid from the connection port 4 to the cannula. For the inner structure of the infusion set (not shown here), e.g. with respect to the way in which the channel is formed between the cannula and the connection port 4 by the first 1 and the second structural part 3 and how the cannula is connected to the first structural part 1, reference is also made to the following embodiments, in which structures are shown in detail and are also suited for this first preferred embodiment.

Figure 6:
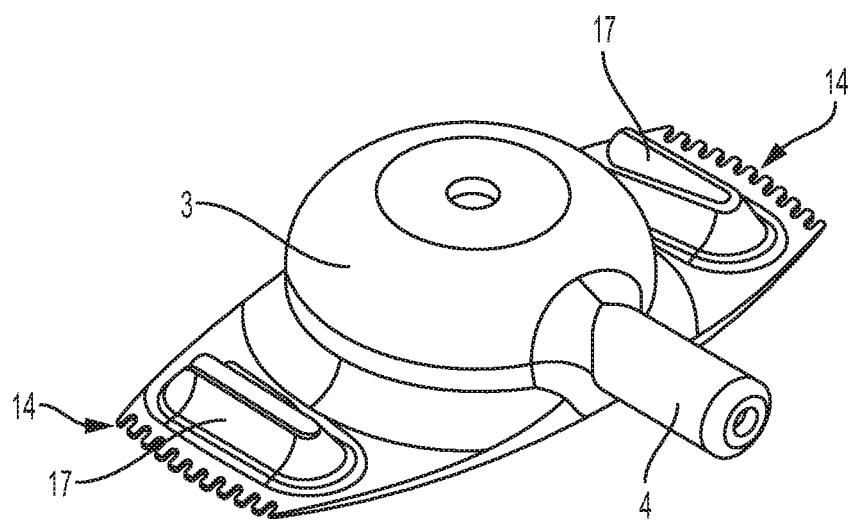
FIG. 6 is a perspective view of the second structural part of the embodiment of FIG. 1 providing the connection port.
Figure 7:
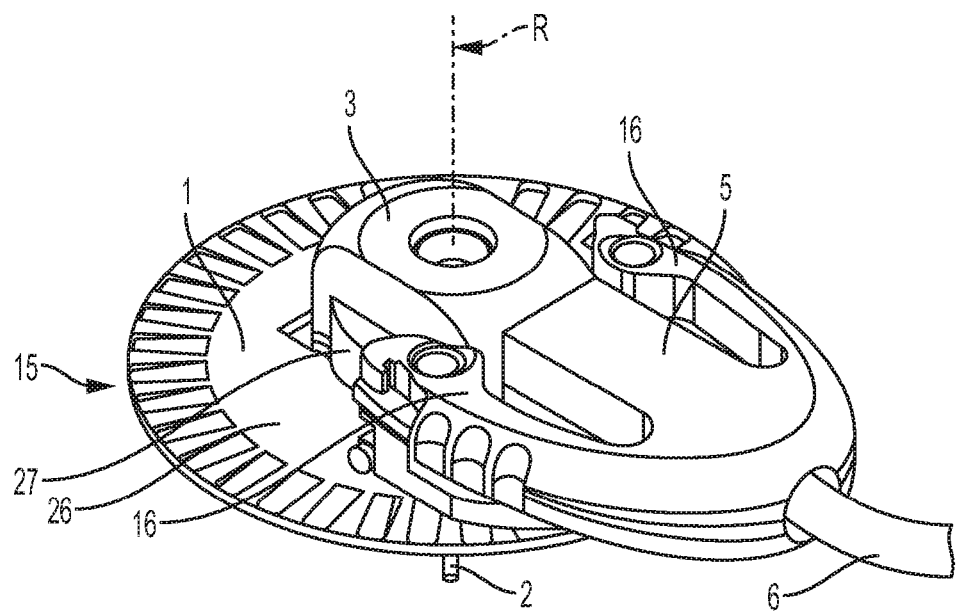
FIG. 7 is a perspective plan view of another embodiment of an arrangement of the present invention in the applied state with a supply conduit connected.

With reference to FIGS. 3, 4 and 6, the second structural part 3 has on the topside of its outermost radial periphery upwardly aligned teeth 14. In the absence of a corresponding connector 5 for coupling the supply conduit 6 to the connection port 4, the teeth 14 engage resiliently in corresponding, opposing teeth 15 under the effect of a spring force generated by the second structural part 3. When the supply conduit is not connected, the spring force overrides the twisting capacity of both structural parts 1, 3 relative to one another (see FIG. 4). If the supply conduit 6 with its connector 5 is coupled to the connection port 4 of the second structural part 3, in that the retaining arms 16 of the connector are moved towards one another, e.g. by exerting pressure with the thumb and index finger, under elastic deformation of the same, the connector 5 is set on the connection port 4 at the same time in a direction vertical to the axis of rotation R of both structural parts 1, 3 or respectively to the longitudinal axis of the cannula. If the retaining arms 16 are then released again, whereby they are moved away again from one another and come up against stop cams 17 on the second structural part 3 under spring preload, the second structural part 3 is bulged or urged downwardly by the spring force of the retaining arms 16 in the vicinity of its external radial periphery, whereby its teeth 14 disengage from the teeth 15 of the first structural part 1 and the structural parts 1, 3 can be rotated against one another. At the same time, when viewed in the direction of coupling of the connector 5, the retaining arms 16 catch behind the stop cams 17, making unintentional withdrawal of the connector 5 from the connection port 4 impossible. If the connector 5 is uncoupled from the infusion set by renewed compression of its retaining arms 16 and simultaneous motion of the same against the direction of coupling, the second structural part 3 bulges, is urged or moves upwardly again in the vicinity of its external radial periphery until its teeth 14 engage resiliently in the teeth 15 of the first structural part 1, thus latching both structural parts 1, 3 in the position assumed.

Figure 8:
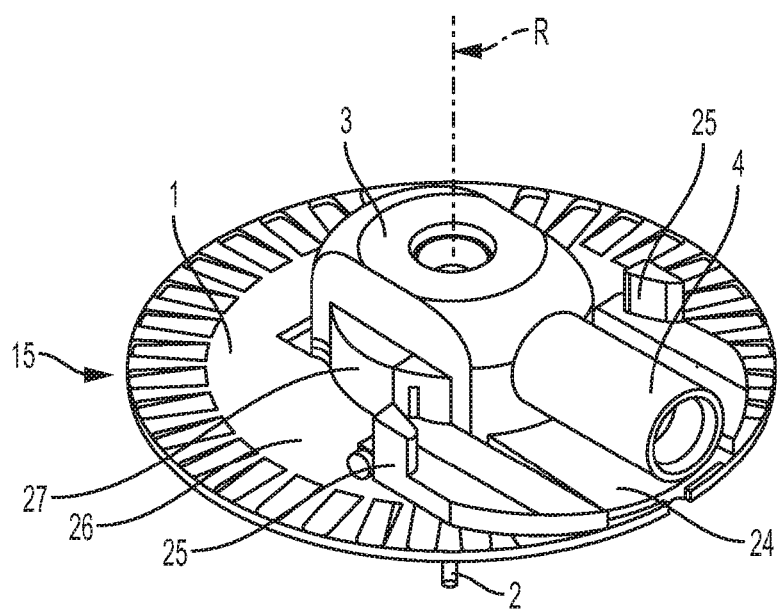
FIG. 8 is a perspective plan view of the embodiment of FIG. 7 without the supply conduit.
Figure 9:
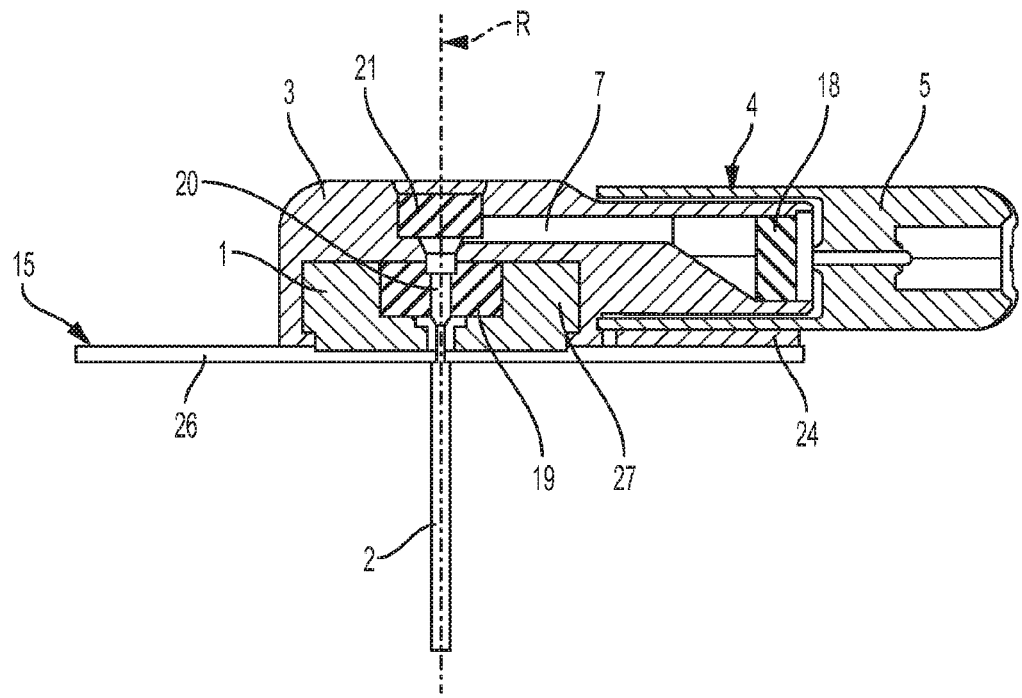
FIG. 9 is a vertical section in the longitudinal direction of the supply conduit through the embodiment illustrated in FIG. 7.
Figure 10:
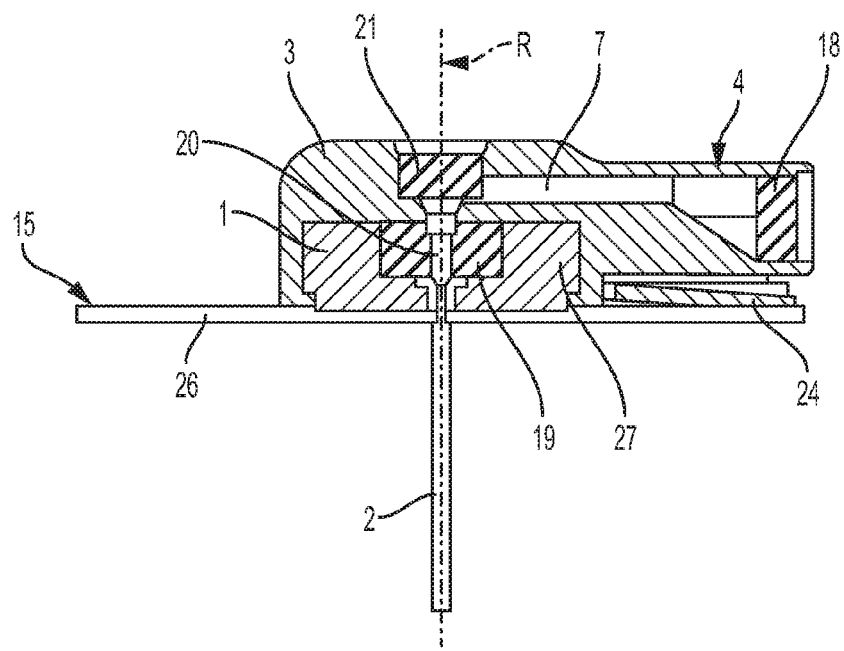
FIG. 10 is an illustration as per FIG. 9 of the embodiment of FIG. 8.
Figure 21:
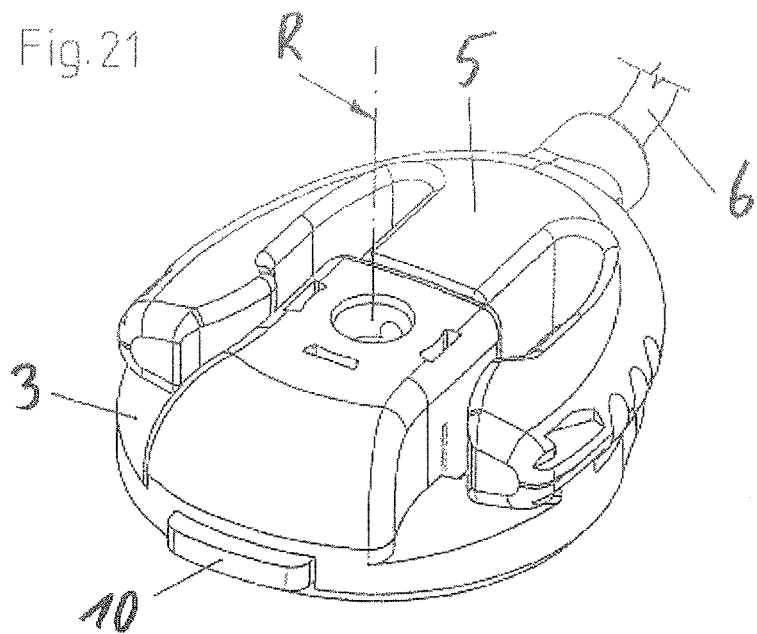
FIG. 21 is a perspective plan view of another embodiment of the present invention in the applied state.
Figure 22:
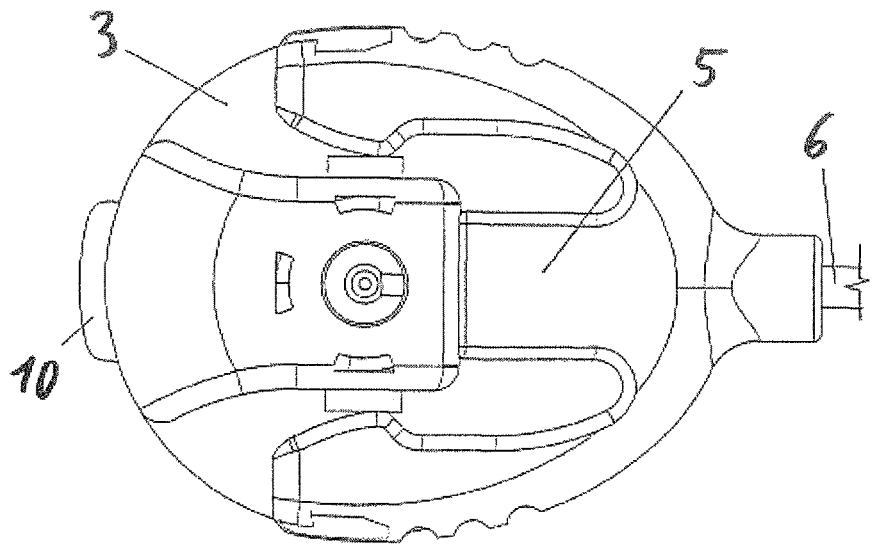
FIG. 22 is a plan view of the embodiment of FIG. 21.

FIGS. 7 to 10 show, in perspective plan views and in longitudinal sections, a second embodiment of the inventive arrangement of the present invention in the form of an applied infusion set, and specifically with coupled supply conduit (FIGS. 7 and 9) and without a supply conduit (FIGS. 8 and 10). The infusion set again has a first structural part 1 which bears on its underside a vertically projecting cannula 2 made of flexible material. Arranged on the topside of the first structural part 1 is a second structural part 3 which forms a connection port 4 for coupling a corresponding connector 5 of a supply conduit 6 for infusion liquid. The first 1 and the second structural part 3 are inseparable and are connected together rotatably relative to one another about a vertical axis of rotation R, whereby the axis of rotation R is identical to the longitudinal axis of the cannula 2. In each rotatory relative position which they can take up relative to one another, the first and second parts form a liquid-tight channel 7 for delivering infusion liquid from the connection port 4 to the cannula 2. As is evident from FIGS. 9 and 10, the channel 7 on the connection port side is delimited or defined in part by a first septum 18 which acts as liquid-tight coupling of the supply conduit 6, in that it is pierced through during coupling of the connector 5 by a delivery cannula (not shown here, however see FIGS. 15 and 18 of the following exemplary embodiments) arranged in the former.

Liquid-tight transition between the first 1 and the second structural part 3 is effected by a second septum 19 provided by the first structural part 1 and penetrated by a cannula extension 20 of the second structural part 3, extending in the axis of rotation R of the structural parts 1, 3. As is evident from FIGS. 11 and 12, which show vertical sections through the arrangement illustrated in FIG. 7, prior to application the arrangement may be in a special protective housing 23a, 23b, and the channel 7 is blocked or sealed directly opposite the inlet aperture of the cannula 2 and in straight-line extension of the cannula channel by another septum 21 which forms part of the topside of the second structural part 3 and is penetrated in the original state by a guide needle 11. This guide needle 11 supports the cannula 2 during application of the infusion set by inserting the cannula 2 into the body of a patient and after application is withdrawn using a reset element 22 arranged at its external end from the cannula channel and the other septum 21 and removed from the infusion set.

The protective housing 23a, 23b is formed from two housing halves 23a, 23b which, based on the original situation illustrated in FIG. 11, in which the infusion set is marketed and in which it is arranged protected inside the housing 23a, 23b, can be telescoped. The first structural part 1 of this embodiment is formed by a circular plate element 26 and a central body 27 bearing the cannula 2 and connected to the second structural part 3, whereby the plate element 26 and the central body 27 are configured to pivot relative to one another. Both housing halves 23a, 23b have guides, via which, during telescoping of the same, the central body 27 is pivoted with the second structural part 3 arranged thereon and the cannula 2 pierced through by the guide needle 11, until the cannula 2 pierced through by the guide needle 11 projects at a right angle from the housing 23a, 23b and from the plate element 26. In this situation, which is illustrated in FIG. 12, both the two housing halves 23a, 23b and also the plate element 26 and the central body 27 snap in undetachably to one another and the housing 23a, 23b forms a grip for a user which is grasped for application of the infusion set and by which the guide needle 11 is withdrawn with the reset element 22 from the cannula 2 and the other septum 21 and removed from the infusion set.

As is further evident from FIGS. 7 to 10, the plate element 26 of the first structural part 1 has on the peripheral delimiting of its topside upward aligned teeth 15, in which a projection formed on the underside of a locking rocker 24 formed by the second structural part 3 engages in the absence of a corresponding connector 5 for coupling the supply conduit 6 to the connection port 4 of the second structural part 3. Thus, the twisting capacity or motion of both structural parts 1, 3 to one another when the supply conduit 6 is not connected is overridden or prevented (see FIGS. 8 and 10). If the supply conduit 6 with its connector 5 is coupled to the connection port 4 of the second structural part 3 by the connector 5 being set on the connection port 4 in a direction vertical to the axis of rotation R of both structural parts 1, 3 or respectively to the longitudinal axis of the cannula 2, whereby its retaining arms 16 latch behind an assigned retainer cam 25 such that unintentional removal of the connector 5 from the connection port 4 is rendered impossible, the locking rocker 24 is deflected by the connector 5. The projection formed on its underside thereby disengages from the teeth 15 of the first structural part 1 and the structural parts 1, 3 can be rotated against one another. If the connector 5 is removed again, for which the retaining arms 16 have to be moved toward one by exertion of pressure by the thumb and index finger for disengaging from the retainer cams 25, while the connector 5 is removed against the direction of coupling from the infusion set, the locking rocker 24 tips supported by spring force back into its previous start position and latches both structural parts 1, 3 in the rotary position relative to one another.

FIGS. 13 to 15 show a third embodiment of an inventive arrangement in accordance with the present invention in the form of an applied infusion set with connected supply conduit, viewed in perspective plan view (FIG. 13), in side elevation from the direction of connection of the supply conduit (FIG. 14) and in the vertical section in the longitudinal direction of the supply conduit (FIG. 15). As is evident from the figures, the infusion set has a first structural part 1, which is formed substantially by a circular plate element 26 and a central body 27 which bears the cannula 2. In the upper region the central body 27 is enclosed by a second structural part 3 in the peripheral sense, which forms a connection port 4 for coupling a corresponding connector 5 of a supply conduit 6 for infusion liquid. The first 1 and the second structural part 3 are inseparable and are connected to one another rotatably relative to one another about a vertical axis of rotation R, whereby the axis of rotation R is identical to the longitudinal axis of the cannula 2.

In each rotatory relative position which they can take up relative to one another, the first 1 and the second structural part 3 form a liquid-tight channel 7 for delivering infusion liquid from the connection port 4 to the cannula 2. As is evident from FIG. 15 the channel 7 is delimited on the connection port side by a first septum 18 which acts as liquid-tight coupling of the supply conduit 6, in that it is pierced through by a delivery cannula 28 arranged therein when the connector 5 is coupled. The liquid-tight transition between the first 1 and the second structural part 3 is effected by two O-rings 31 spaced apart from one another in the longitudinal direction of the cannula 2, which are borne or carried by the central body 27. Between these O-rings 31 the central body 27 has a peripheral groove 29 which is connected via a radial bore 30 to the cannula entry. The channel 7 is delimited directly opposite the inlet aperture of the cannula 2 and in straight-line extension of the cannula channel by another septum 21 which forms part of the topside of the central body 27 of the first structural part 1 and in the original state is penetrated by a guide needle (not shown here). This guide needle supports the cannula 2 when inserted into the body of a patient and after application is withdrawn from the cannula channel and the septum 21 and removed from the infusion set.

Referring to FIG. 13, the plate element 26 of the first structural part 1 has on its topside six identical, trough-like depressions 32 arranged evenly spaced generally peripherally, whereof the surface contour has a constant profile cross-section when viewed in a radial direction. As is evident from FIG. 14, the assigned connector 5 of the supply conduit 6 has on its underside a corresponding countercontour and is guided on the connection port 4 of the second structural part 3 such that it can be set on the connection port 4 and then latches the structural parts 1, 3 in a relative position. The connection port 4 is located in the middle above one of the depressions 32, in that it engages with the countercontour of its underside in the respective depression 32. In this embodiment, the first 1 and the second structural part 3 can be latched in six different rotatory positions relative to one another, whereby coupling of the connector 5 to the connection port 4 is possible only in one of these relative positions, inevitably resulting in latching of the structural parts 1, 3 in the relative position. Here, too, the connector 5 has retaining arms 16, with which it snaps in behind retainer cams (not shown) when being set on the connection port 4, preventing unintentional removal of the connector 5 from the connection port 4. The arms have to be moved toward one another for uncoupling the connector 5 from the infusion set by exertion of pressure by the thumb and index finger, so that the connector 5 can be removed against the direction of coupling. As previously described, if the connector 5 is again removed from the infusion set both structural parts 1, 3 can be rotated again relative to one another.

FIGS. 16 to 18 show a fourth embodiment in accordance with the present invention in the form of an applied infusion set. The set is shown in perspective plan view with a connected supply conduit (FIG. 16), in perspective plan view without the supply conduit (FIG. 17) and in the vertical section in the longitudinal direction of the connected supply conduit (FIG. 18). The infusion set shown here has a similar construction as that previously described, however with the difference that here the plate element 26 is designed in one piece with the central body 27 and on its topside, instead of the six large depressions along its peripheral limit, it has a multiplicity of identical small depressions 32, arranged evenly spaced in the peripheral sense, resulting in the vicinity of the edge having a corrugated surface contour. Likewise in contrast to the previous embodiment, the second structural part 3 here has a spring-elastic latching arm 33, which, when the supply conduit 6 is not connected to a detent projection 34 formed on its underside, rests on the corrugated surface contour of the plate element 26 and thus together with the latter forms a ratchet mechanism, the effect of which is that a specific force must be applied to rotate the second structural part 3 relative to the first structural part 1 and that these structural parts 1, 3 in each case assume discrete positions relative to one another.

If a corresponding connector 5 is set on the connection port 4 of the second structural part 3, as shown in FIGS. 16 and 18, the latching arm 33 is prevented by the connector 5 from deviating upward and the first 1 and the second structural part 3 are latched in their relative position. In this embodiment, the first 1 and the second structural part 3 can therefore be latched in a multiplicity of discrete positions relative to one another, whereby coupling of the connector 5 to the connection port 4 is possible only in one of these relative positions, inevitably resulting in latching of the structural parts 1, 3 in the relative position. When the connector 5 is disconnected, the first 1 and the second structural part 3 can be rotated against one another against a force defined by the previously described ratchet mechanism, whereby they assume discrete positions relative to one another after a torsional force has been overcome. Here, too, the connector 5 has retaining arms 16, with which it snaps in behind retainer cams 25 when set on the connection port 4, rendering unintentional removal of the connector 5 from the connection port 4 impossible. The arms have to be moved toward one another to uncouple the connector 5 from the infusion set, so that the connector 5 can be removed against the direction of coupling. The remaining construction of this embodiment, with respect to the structural design of the seals 18, 21, 31 and the channel 7, corresponds substantially to the previous embodiment. Those elements not described explicitly here, though provided with reference numerals, have the same function as the structural parts with corresponding reference numerals in the previously described designs.

FIGS. 19 and 20 show a fifth embodiment of the present invention in the form of an applied infusion set. The set is shown in perspective plan view with a connected supply conduit (FIG. 19) and in the vertical section in the longitudinal direction of the connected supply conduit (FIG. 20). The infusion set shown here is identical to that previously described, with the difference that here the latching arm 33 is arranged at a peripheral position opposite the connection port and, as a result, can also rebound when the supply conduit 6 is connected. In this embodiment, the second structural part 3 can accordingly always be rotated against the force defined by the ratchet mechanism relative to the first structural part 1, both when the connector 5 is coupled and also when the connector 5 is removed, whereby the structural parts 1, 3 then assume positions relative to one another. Those elements not described explicitly here, though provided with reference numerals, have the same function as the structural parts with corresponding reference numerals in the previously described design.

FIGS. 21 to 24 show another embodiment of the present invention in the form of an applied infusion set with a connected supply conduit. The set is shown in perspective plan view (FIG. 21), in plan view (FIG. 22), in side elevation (FIG. 23) and in vertical section in the longitudinal direction of the connected supply conduit (FIG. 24). The inner construction of this embodiment with respect to the structural configuration of the seals 8, 18 and 21 of the channel 7 corresponds substantially to the second embodiment discussed with reference to FIGS. 7 to 10.

As is evident from FIGS. 21 to 24 the infusion set again has a first structural part 1, which on its underside bears a vertically projecting cannula 2 made of flexible material. On the topside of the first structural part 1 a second structural part 3 is arranged, and forms a connection port 4 for coupling a corresponding connector 5 of a supply conduit 6 for infusion liquid. The first 1 and the second structural part 3 are inseparably connected to one another and can be rotated relative to one another about a vertical axis of rotation R, whereby the axis of rotation R is identical to the longitudinal axis of the cannula 2. In each rotary relative position which they can assume relative to one another, the first and second parts form a liquid-tight channel 7 for delivering infusion liquid from the connection port 4 to the cannula 2. Here, too, the channel 7 is delimited or defined in part on the connection port side by a first septum 18 which serves as liquid-tight coupling of the supply conduit 6, in that it is pierced through during coupling of the connector 5 by a delivery cannula 28 arranged therein. The liquid-tight transition between the first 1 and the second structural part 3 is effected by a rubber seal 8 under compressive stress, which is penetrated by a connection journal 9 of the second structural part 3, extending in the axis of rotation R of the structural parts 1, 3 and which has in its center a bore forming part of the channel 7. Directly opposite the inlet aperture of the bore of the journal 9 and in straight-line extension of the cannula channel the channel 7 is delimited by another septum 21 which forms part of the topside of the second structural part 3 and in the original state is penetrated by a guide needle (not shown). This guide needle supports the cannula 2 in application of the infusion set by insertion of the cannula 2 into the body of a patient and after application is withdrawn from the cannula channel and the other septum 21 by a reset element arranged on its external end and is removed from the infusion set.

FIG. 25 shows a perspective view of the first structural part 1 together with an actuating element 10 of a latching device. The first structural part 1 is formed from a plate element 26, which has circular, radially inwardly directed inner cogging 15, and a central body 27 which in the center of the plate element 26 projects upwardly therefrom. Arranged between the first 1 and the second structural part 3 in a peripheral position, lying opposite the connection port 4, is the actuating element 10, which is guided radially in the second structural part 3 and is pressed radially outwardly with a spring tab 35 formed by the second structural part 3 with spring preload. Thus, it engages with corresponding counter-cogging (not shown) formed by the latter in the inner cogging 15 of the first structural part 1, thereby preventing rotating of both structural parts 1, 3 in the illustrated situation. If a compressive force is exerted on the actuating element 10 inwardly in a radial direction, then it shifts against the spring force of the spring tab 35 radially inwardly, whereby the counter-cogging of the actuating element 10 is disengaged from the inner cogging 15 and twisting of the second structural part 3 relative to the first structural part 1 becomes possible, independently of whether or not a connector 5 is coupled to the connection port 4. If the actuating element 10 is released it is again moved radially outwardly by the spring tab 35 until the counter-cogging of the actuating element 10 engages in the inner cogging 15 of the first structural part 1 and latches both structural parts 1, 3 in the rotatory relative position. Here also the latching is carried out at discrete positions.

Embodiments of the present invention, including preferred embodiments, have been presented for the purpose of illustration and description. They are not intended to be exhaustive or to limit the invention to the precise forms and steps disclosed. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A method for delivering a therapeutic substance to a patient, the method comprising:
   providing a device comprising a connector of a conduit for carrying the therapeutic substance, a first structural part with a cannula extending therefrom for positioning in a body of the patient and formed by a plate element and a central body, a second structural part with a connection port for detachably coupling to the connector of the conduit, wherein the first structural part and the second structural part are connected to one another such that they are inseparable, can be rotated relative to one another and in a selected rotational position to form a channel for introducing the therapeutic substance from the connection port to the cannula, and wherein the connection port is designed such that the movement of the coupling and uncoupling of the conduit takes place in a direction transverse to the longitudinal axis of the cannula, and wherein the second structural part has a spring-elastic latching arm which rests on a corrugated surface contour of the plate element to form a ratchet mechanism such that the first structural part and second structural part can be rotated relative to one another when the connector is not set on the connection port; and applying the device to the patient's body so that the cannula is positioned in the body;

operably coupling a supply of the therapeutic substance to the conduit; and causing the therapeutic substance to flow into the patient's body.

2. The method of claim 1, wherein the therapeutic substance is insulin.

3. A method for introducing a liquid to a body of a patient or for withdrawing the liquid from the body of the patient, comprising:

providing an arrangement for introducing the liquid to the body of the patient or for withdrawing the liquid from the body of the patient, the arrangement comprising:
 a connector of a conduit for supplying or withdrawing the liquid, the conduit coupled to a delivery cannula;
 a first structural part with a cannula protruding therefrom for arrangement in the body of the patient, the first structural part formed by a circular plate element and a central body; and
 a second structural part with a spring-elastic latching arm coupled to a connection port for detachable coupling of the connector;
wherein the first structural part and the second structural part are configured and connected to one another such that they can be rotated relative to one another and in every relative position to form a channel for introducing the liquid from the connection port to the cannula or for withdrawing a liquid from the cannula to the connection port, and wherein the conduit and the cannula are connected by the channel beginning at a distal end of the conduit and ending at a proximal end of the cannula;
wherein the connection port is designed such that the coupling and uncoupling of the connector associated with the conduit takes place in a direction transverse to the longitudinal axis of the cannula, and wherein the channel extends from an end of the delivery cannula which is farthest from the conduit, extending in the direction transverse to the longitudinal axis of the cannula to provide a liquid-tight connection between the cannula and the end of the delivery cannula which are separated in the direction transverse to the longitudinal axis of the cannula; and
the connector comprises opposing retaining arms configured such that when the connector is set on the connection port, the retaining arms catch behind opposing stop cams which comprise projections extending up from the second structural part to substantially prevent unintentional uncoupling of the connector, and the connector prevents the latching arm from deviating upward and the first and the second structural parts are latched in a position; and the spring-elastic latching arm rests on a corrugated surface contour of the plate element to form a ratchet mechanism such that the first structural part and second structural part can be rotated relative to one another when the connector is not set on the connection port; and rotating the first structural part and the second structural part relative to one another when the connector is not set on the connection port; and introducing the liquid into the body of the patient or withdrawing the liquid from the body of the patient via the arrangement.

4. The method of claim 3, further comprising rotating the first and the second structural part relative to one another about an axis of rotation extending parallel to the longitudinal axis of the cannula.

5. The method of claim 3, further comprising projecting the cannula vertically or non-vertically from a substantially flat outside surface of the first structural part and rotating the first and the second structural part relative to one another by an axis of rotation extending vertically to the surface.

6. The method of claim 3, further comprising rotating the first and the second structural part relative to one another by one of 360° or less than 360°.

7. The method of claim 3, further comprising arranging the connection between the first and the second structural part such that a specific torque must be overcome for counterrotation of said structural parts.

8. The method according to claim 7, further comprising overcoming the torque, the torque ranging between about 0.01 Newton meters (Nm) and about 0.05 Nm.

9. The method according to claim 7, further comprising overcoming the torque, the torque ranging between about 0.01 Newton meters (Nm) and about 0.1 Nm.

10. The arrangement as claimed in claim 7, further comprising generating the torque to be overcome via a pre-tensed elastic seal.

11. The method of claim 3, further comprising forcing a removable guide needle through the cannula so as to enable the cannula to be inserted into a tissue of the patient.

12. The method of claim 11, further comprising fastening the first structural part to a skin of the patient via an adhesive layer.

13. The method of claim 3, further comprising coupling, via another connector, another conduit for supplying or withdrawing the liquid.

14. The method of claim 3, further comprising deforming the retaining arms.

15. A method for introducing a liquid to a body of a patient or for withdrawing the liquid from the body of a patient, the method comprising:

providing an arrangement for introducing the liquid to the body of the patient or for withdrawing the liquid from the body of the patient, comprising:
 a connector of a conduit for supplying or withdrawing the liquid, the connector comprising a delivery cannula;
 a first structural part comprising a cannula protruding therefrom for arrangement in the body of the patient, the first structural part formed by a circular plate element and a central body; and
 a second structural part with a spring-elastic latching arm coupled to a connection port for detachable coupling of the connector, the connection port forming a portion of a fluid path to the cannula, wherein the first structural part and the second structural part are configured and connected to one another such that they can be rotated relative to one another and in every relative position to form a channel for introducing a liquid from the connection port to the insertion cannula or for withdrawing a liquid from the cannula to the connection port, and wherein the conduit and the cannula are connected by the channel beginning at a distal end of the conduit and ending at a proximal end of the cannula, and wherein the channel extends from an end of the delivery cannula which is farthest from the conduit, extending in the direction transverse to the longitudinal axis of the cannula to provide a liquid-tight connection between the cannula and the end of the delivery cannula which are separated in the direction transverse to the longitudinal axis of the cannula;

wherein the connection port is configured such that the connector and delivery cannula are coupled thereto in the direction transverse to the longitudinal axis of the cannula; and wherein the connector comprises opposing retaining arms configured such that when the connector is set on the connection port, the retaining arms catch behind opposing stop cams which comprise projections extending up from the second structural part to substantially prevent unintentional uncoupling of the connector, and the connector prevents the latching arm from deviating upward and the first and the second structural parts are latched in a position; and the spring-elastic latching arm rests on a corrugated surface contour of the plate element to form a ratchet mechanism for the relative rotation of the first structural part and the second structural part when the connector is not set on the connection port; and rotating the first structural part and the second structural part relative to one another when the connector is not set on the connection port; and introducing the liquid into the body of the patient or withdrawing the liquid from the body of the patient via the arrangement.

16. The method of claim 15, further comprising sealing the fluid path via a septum and piercing, via the delivery cannula, the septum in a direction substantially transverse to the longitudinal axis of the cannula upon coupling of the connector to the connection port.

17. The method of claim 15, further comprising deforming the retaining arms between a compressed position in which the connector is coupled to the connection port and a relaxed position in which the retaining arms engage the stop cams.

* * * * *

UNITED STATES PATENT AND TRADEMARK OFFICE
CERTIFICATE OF CORRECTION

PATENT NO. : 9,744,295 B2  
APPLICATION NO. : 14/948714  
DATED : August 29, 2017  
INVENTOR(S) : Martin Wyss et al.

Page 1 of 1

It is certified that error appears in the above-identified patent and that said Letters Patent is hereby corrected as shown below:

On the Title Page

(72) Inventors: "Martin Wyss, Burgdorf (CH)  
Simon Scheuer, Bern (CH);  
Reto Aeschilmann, Aefligen (CH);  
Christian Thalmann, Kehrsiten (CH)"  
Should read:  
(72) Inventors: --Martin Wyss, Burgdorf (CH)  
Simon Scheuer, Bern (CH);  
Reto Aeschlimann, Aefligen (CH);  
Christian Thalmann, Kehrsiten (CH)--;

(73) Assignee: "Roche Diagnostics International AG, Steinhausen (CH)"  
Should read:  
(73) Assignee: --Roche Diabetes Care. Inc., Indianapolis (US)--.

Signed and Sealed this  
Nineteenth Day of June, 2018

Andrei Iancu  
*Director of the United States Patent and Trademark Office*